United States Patent [19]

Seltzer

[11] Patent Number: 5,986,757
[45] Date of Patent: Nov. 16, 1999

[54] CORRECTION OF SPECTRAL INTERFERENCES ARISING FROM CN EMISSION IN CONTINUOUS AIR MONITORING USING INDUCTIVELY COUPLED PLASMA ATOMIC EMISSION SPECTROSCOPY

[75] Inventor: Michael D. Seltzer, Ridgecrest, Calif.

[73] Assignee: The United States of America as represented by the Secretary of the Navy, Washington, D.C.

[21] Appl. No.: 08/932,023

[22] Filed: Sep. 17, 1997

[51] Int. Cl.[6] .......................... G01N 21/63; G01N 21/72; G01N 21/73; G01J 3/443

[52] U.S. Cl. .......................... 356/307; 356/315; 356/316; 356/318

[58] Field of Search .................................. 356/307, 316, 356/315, 318

[56] References Cited

U.S. PATENT DOCUMENTS

| Re. 29,304 | 7/1977 | Greenfield et al. . |
| 3,965,747 | 6/1976 | McCorkle . |
| 3,965,748 | 6/1976 | Boubel et al. . |

(List continued on next page.)

OTHER PUBLICATIONS

J.D. Chase Theoretical and Experimental Investigation of Pressure and Flow in Induction Plasmas, Journal of Applied Physics. Nov. 1971 vol. 42, No. 12, pp. 4870–4879.

D. Truitt & J.W.Robinson Spectroscopic Studies of Organic Compounds Introduced into a Radio Frequency Induced Plasma. Analytica Chemica Acta, 51–1970 pp. 61–67 Elsevier Publishing Company, Amsterdam.

Seltzer, Michael D. An Argon ICP–Based Continuous Emissions Monitor for Hazardous Air Pollutant Metals: Field Demonstration Presentation of the Ari Waste Management Association. 90th Annual Management Exhibition.

Seltzer, Michael D. An Inductively Coupled Argon Plasma Continuous Emissions Monitor forHazardous Air Pollutant Metals, Environmental Science and Technology Sep. 1997. Submitted Apr. 1997.

Seltzer, Michael D & Gerhard A. Meyer, Keeping and Eye on Metals Emissions, Environmental Protection , Jun. 1997 vol. 8 No. 6—pp. 26–29.

Seltzer, Michael D. Continuous Air Monitoring Using Inductively Coupled Plasma, Applied Spectroscopy, Submitted Jun. 1997.

Emmisions Measurement Branch, nsps Test Method, EMTIC M–002 Technical Support Division , OAQPS, EPA, NAWS China Lake.

*Primary Examiner*—F. L. Evans
*Attorney, Agent, or Firm*—Gregory M. Bokar; David S. Kalmbaugh

[57] ABSTRACT

Introduction of sample stream air into argon inductively coupled plasma permits continuous monitoring of hazardous air pollutant metals in combustion flue gases. In addition to entrained particulates, various molecular components of flue gas are in the plasma. These species, and reaction products thereof, such as CN species, also undergo excitation resulting in complex emission spectra of appreciable intensity. Serious spectral interference arises for several metal elements, from molecular emission bands associated with the stable CN radical, and other poly-atomic species, such as NO. Failure to account for these interferences can significantly degrade accuracy of monitoring particularly at low metal concentrations in the flue gas. This invention corrects spectral interferences arising from airborne molecular species in the argon plasma even when the magnitudes of spectral interferences encountered during the analysis of airborne metals in flue gases, are of such considerable magnitudes that, if not directly accounted for, would otherwise compromise the quality of measurements of the airborne metals. This method measures and corrects spectral interferences attributed to CN and NO that affect on-line detection of hazardous air pollutant metals. The method incorporates conventional spectrometer hardware and existing instrument software to achieve effective real-time correction of these interferences.

33 Claims, 7 Drawing Sheets

U.S. PATENT DOCUMENTS

| | | |
|---|---|---|
| 4,091,835 | 5/1978 | Frampton . |
| 4,159,635 | 7/1979 | Sehmel . |
| 4,293,220 | 10/1981 | Denton et al. . |
| 4,390,772 | 6/1983 | Hiratake . |
| 4,482,246 | 11/1984 | Meyer et al. . |
| 4,566,342 | 1/1986 | Kurz . |
| 4,649,760 | 3/1987 | Wedding . |
| 4,739,147 | 4/1988 | Meyer et al. . |
| 4,851,683 | 7/1989 | Yang et al. ............................. 356/316 |
| 5,009,099 | 4/1991 | Wells et al. ............................. 356/307 |
| 5,012,065 | 4/1991 | Rayson et al. . |
| 5,090,257 | 2/1992 | Bruce . |
| 5,479,254 | 12/1995 | Woskov et al. . |
| 5,526,110 | 6/1996 | Braymen . |

TABLE I. ANALYTICAL WAVELENGTHS

| ELEMENT | WAVELENGTH | ELEMENT | WAVELENGTH |
|---|---|---|---|
| ALUMINUM | 308.215 | IRON | 292.969 |
| ANTIMONY | 206.838* | LEAD | 220.353* |
| ARSENIC | 189.042* | MANGANESE | 257.610 |
| BARIUM | 493.409 | MERCURY | 184.950 |
| BERYLLIUM | 313.042 | NICKEL | 231.604* |
| CADMIUM | 226.502 | SELENIUM | 196.026* |
| CHROMIUM | 267.716 | SILVER | 328.068 |
| COBALT | 228.616 | THALLIUM | 190.864* |

*2nd ORDER

FIG. 2A

TABLE II. EFFECTIVENESS OF CORRECTION FOR CN SPECTRAL INTERFERENCE

| ANALYTE | DETECTION LIMIT (μg/DSCM) | IEC COEFFICIENT* | PERCENT $CO_2$ | ANALYTE CONCENTRATION (μg/DSCM) | | PERCENT CORRECTION |
|---|---|---|---|---|---|---|
| | | | | APPARENT | CORRECTED | |
| Ag | 1.1 | -3.505 | 5.27 | -19.0 | -0.524 | 95% |
| | | | 9.91 | -36.2 | -1.42 | 96% |
| As | 8 | 18.425 | 5.27 | 95.2 | -2.60 | 103% |
| | | | 9.91 | 182 | -1.39 | 101% |
| Hg | 10 | -19.779 | 5.27 | -101 | 3.62 | 104% |
| | | | 9.91 | -195 | 0.828 | 100% |
| Pb | 2.5 | 2.641 | 5.27 | 11.6 | -1.66 | 114% |
| | | | 9.91 | 25.6 | 0.728 | 97% |
| Sb | 7 | 2.042 | 5.27 | 12.5 | 2.84 | 77% |
| | | | 9.91 | 20.2 | 2.23 | 89% |
| Se | 10 | 37.705 | 5.27 | 198 | 2.73 | 106% |
| | | | 9.91 | 375 | 1.79 | 100% |
| Ti | 20 | 43.172 | 5.27 | 248 | 20.1 | 92% |
| | | | 9.91 | 420 | -7.58 | 102% |

*IEC COEFFICIENTS DETERMINED USING 10 PERCENT $CO_2$ INTRODUCTION

FIG. 2B

CORRECTION OF SPECTRAL INTERFERENCES ARISING FROM CN EMISSION IN CONTINUOUS AIR MONITORING USING INDUCTIVELY COUPLED PLASMA ATOMIC EMISSION SPECTROSCOPY

CROSS REFERENCE TO RELATED APPLICATIONS

This application is related to U.S. patent applications entitled "Modified Plasma Torch Design for Introducing Sample Air into Inductively Coupled Plasma" by Michael Seltzer in the U.S. Patent and Trademark Office U.S. patent application Ser. No. 08/932,397, filed Sep. 17, 1997, now U.S. Pat. No. 5,908,566, and "Sampling Interface for Continuous Monitoring of Emissions" by Michael Seltzer, U.S. Patent and Trademark Office U.S. patent application Ser. No. 08/932,233, filed Sep. 17, 1997, now U.S. Pat. No. 5,834,656, and "Method and Apparatus for Automated Isokinetic Sampling of Combustor Flue Gases for Continuous Monitoring of Hazardous Metal Emissions" by Michael Seltzer, U.S. Patent and Trademark Office U.S. patent application Ser. No. 08/932,401, filed Sep. 17, 1997, now U.S. Statutory Invention Registration No. H001757, and incorporates all references and information thereof by reference herein.

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION

Conventional atomic emission spectrometry, where samples to be analyzed are usually liquids or solids, has had to deal with spectral interferences that most often arose from light emitted by other metals present at high concentrations in the sample. The spectral interference most often results in an erroneous analysis for the element of interest due to spectral contributions from the interfering element at the detection wavelength of the element of interest. If the source (element) of the interfering emission can be identified, certain steps can be taken to account for the interference and minimize or eliminate any attendant effects.

However, continuous emissions monitoring for hazardous air pollutant metals is an emerging technology. Prior to this time, there has been no documentation reporting a satisfactory solution to correcting the problems associated with this monitoring. This is primarily because performance limitations of existing instrumentation did not permit detection of airborne metals at sufficiently low concentrations where molecular gas emissions would be considered a problem. The goals of developing a continuous emissions monitor for airborne metals having low sensitivity and accurate measurements at these low levels have not been met heretofore. One approach used by the applicant was to apply post measurement calculations in an attempt to correct for the type of molecular gas spectral interferences described above. This approach is neither accurate nor does it support real-time measurement. No other prototype technology for continuous monitoring of airborne metal emissions is sufficiently sensitive so that the issue of molecular gas spectral interference must be contended with.

Several prototype technologies have been attempted in recent years to address the need for instrumentation and methodology capable of continuous, real-time measurement of hazardous air pollutant (HAP) metals in the flue gases of large scale combustors such as waste incinerators, cement kilns, and coal-and-oil-fired power plants. Among these, however, a noteworthy continuous emissions monitor (CEM) has evolved that is based on the introduction of sample stream air into an argon inductively coupled plasma (ICP) and has been most successful in fulfilling the requirements of this demanding application. This CEM is described in U.S. Pat. No. 5,596,405 and monitors hazardous air pollutant metals. In summary, the patent describes a sample air stream that is extracted from an incinerator stack or other duct to be monitored, and introduced into an ICP spectrometer via a device henceforth referred to as a sampling interface. The ICP in this case serves as the actual metal analyzer and is capable of differentiating between various metal pollutants and determining directly, their concentration in the sample air stream. In the plasma, metal atoms are vaporized and excited. This excitation could take place in any number of sources including, but not limited to, inductively coupled argon plasmas, inductively coupled plasma sustained on gases other than argon, microwave-induced plasmas, electrical spark plasmas, arc-induced plasmas, laser-induced plasmas and analytical combustion flames. Once the metal atoms are vaporized and excited by one of the above sources the emission of characteristic wavelengths of light results. A suitable spectrometer is used to differentiate between the various light wavelengths while at the same time, discriminating against background emission of light from the plasma itself. Most metal elements emit light at several wavelengths simultaneously due to the multiplicity of atomic energy levels associated with a given element. The patent adopts a customary practice and selects the most intense emission wavelength for each element for the purpose of obtaining maximum measurement sensitivity. The patented method involves continuous extraction of sample air from a smokestack under strictly isokinetic conditions and frequent, periodic injection of aliquots of that sample air directly into the argon plasma using a plasma torch specifically designed for this application. As presently configured, the CEM of the patent is capable of sensitive, simultaneous analysis of all of the HAP metals at 1–2 minute intervals. Detection limits less than 1 microgram per dry standard cubic meter (DSCM) are routinely achieved for many of the HAP metals. Detection limits are achieved for all HAP metals, well below present or proposed regulatory compliance emission limits for incinerators and cement kilns, see "Revised Standards for Hazardous Waste Combustors, Proposed Rules," *Federal Register*, Apr. 19, 1996, Vol. 61, No. 77, p 17357–17536. Because, any monitors must comply to these regulations for this technology, a particularly high value is placed on measurement accuracy. Spectral interferences can easily compromise accuracy in any spectrochemical technique, and this, unfortunately, was found to be especially true in the patented monitor. The reason for the compromise in accuracy was primarily due to fact that the flue gases of furnaces and incinerators typically contain elevated levels of water vapor, molecular species, such as $CO_2$, $CO$, $NO_x$, and other products of incomplete combustion in addition to metallic and organic pollutants. Introduction of these molecular species into the argon plasma was an unavoidable consequence of air sampling in the patented monitor. In addition, introduction of molecular species into an inductively coupled plasma often resulted in complex thermodynamic perturbation of the plasma, see Trassy, C. C., Diemiaszonek, R. C., *J. Anal. Atomic Spectrosc.*, 9, 661 (1995). During the development and initial field evaluation of the patented CEM, the effects of molecular species on the argon plasma, including spectral interferences and suppression of atomic excitation, have been observed.

Thus, in accordance with this inventive concept, a need has been recognized in the state of the art for a method of monitoring air borne atomic metals by which spectral interferences due to molecular species are corrected to result in accurate measurement of the affected metals.

SUMMARY OF THE INVENTION

The present invention is directed to providing a method of analyzing materials entrained in sample air. Quantifying spectral interference signals attributed to light emitted at some wavelengths characteristic of molecular species that coincide with light emitted at wavelengths characteristic of atomic metals precedes subtracting the spectral interference signals from composite signals representative of said molecular species and said atomic metals to provide difference signals representative of concentrations of the atomic metals in the sample air. Quantifying includes multiplying molecular species concentrations with interference coefficients to account for the spectral interference signals.

Application of the method described in the present invention, correction of spectral interferences arising from molecular gases, while initially demonstrated and practiced using an argon inductively coupled plasma spectrometer is not limited to this specific source of excitation. Other sources of excitation in which this invention is applicable include, but are not limited to, inductively coupled plasma sustained on gases other than argon, microwave-induced plasmas, electrical spark plasmas, arc-induced plasmas, laser-induced plasmas and analytical combustion flames.

An object of the invention is to provide a method for monitoring emissions of hazardous air pollutants.

Another object of the invention is to provide a method for monitoring emissions of hazardous air pollutants in the presence of molecular species.

Another object of the invention is to provide a method for detection of airborne metals at sufficiently low concentrations where molecular gas emissions otherwise would be a problem.

Another object of the invention is to provide a method to quantify and correct for spectral interferences to ensure accurate analyses at lowest airborne metal concentrations detectable by the metals' CEM Another object of the invention is to reduce the problems associated with continuous monitoring of metal emissions in molecular emission bands that directly overlap some of the most intense wavelengths at which atomic emissions from airborne metals are detected.

Another object of the invention is to provide a method for eliminating spectral interferences attributed to molecular species emitting in the same spectrum as atomic metals of interest.

Another object of the invention is to account for CN and other species, such as NO emissions in argon plasma to improve detection of CEM.

Another object of the invention is to remove interferences attributed to CN species in argon plasma to improve detection of concentration of atomic metals.

Another object of the invention is to provide a method of measuring spectral interferences affecting on-line detection of atomic metals.

Another object of the invention is to provide a method of using $CO_2$ as a surrogate source to produce CN emission in plasma for the analysis of constituents of sample air.

Another object of the invention is to provide a method of measuring CN emission intensities arising from the introduction of sample air into plasma and relating those intensities to corresponding $CO_2$ concentrations for the analysis of constituents of the sample air.

Another object of the invention is to provide a method of generating empirical interference coefficients representing the ratio of molecular species concentrations to apparent concentrations for each affected atomic metals.

Another object of the invention is to provide a method for applying empirical interference coefficients to account for contributions of molecular spectral interferences to apparent metal concentrations and to determine net concentrations of affected atomic metals in sample air.

Another object of the invention is to provide a method for continuous monitoring of hazardous air pollutant metals in combustion flue gases.

Another object of the invention is to provide a method that provides for measurement and correction of spectral interferences attributed to CN and NO that affect the on-line detection of hazardous air pollutant metals Another object of the invention is to provide a method that incorporates conventional spectrometer hardware and existing instrument software capabilities to achieve virtually complete correction of spectral interferences in the field.

These and other objects of the invention will become more readily apparent from the ensuing specification when taken in conjunction with the appended claims.

BRIEF DESCRIPTION OF THE DRAWINGS

FIGS. 2A and 2B are tables I and II depicting characteristic emissions of metals and other parameters of interest.

DESCRIPTION OF THE PREFERRED EMBODIMENT

In accordance with this invention, an observation was observed when airborne metals in the flue gases of waste combustors were being analyzed using inductively coupled plasma atomic emission spectrometry as described in U.S. Pat. No. 5,596,405. That observation was that carbon dioxide (a by-product of combustion) also enters the inductively coupled plasma and is decomposed to its atomic constituents, carbon and oxygen. This decomposed carbon was found to be available to react in the argon plasma with nitrogen, an additional component of the sample air stream to form a stable radical, CN species. When the CN species radical was then excited by the argon plasma, emission of light at numerous wavelengths over a wide spectral range resulted. It was further observed that many of the emission wavelengths of the CN radical overlapped the emission wavelengths of the airborne metals being analyzed for. Consequently, the CN emission gave rise to false signals, for the affected metal elements, that are commonly referred to as spectral interferences. These types of spectral interferences would be common to any spectral analytical technique involving direct excitation of the sample gas. In some cases, these spectral interferences were intolerable since they had appreciable magnitudes and could severely affect the accuracy of the metal measurements.

The method which corrects for the problems identified herein is implemented by hardware and software that is appropriately modified to effect the salient features and objects herein described.

Figure 1:
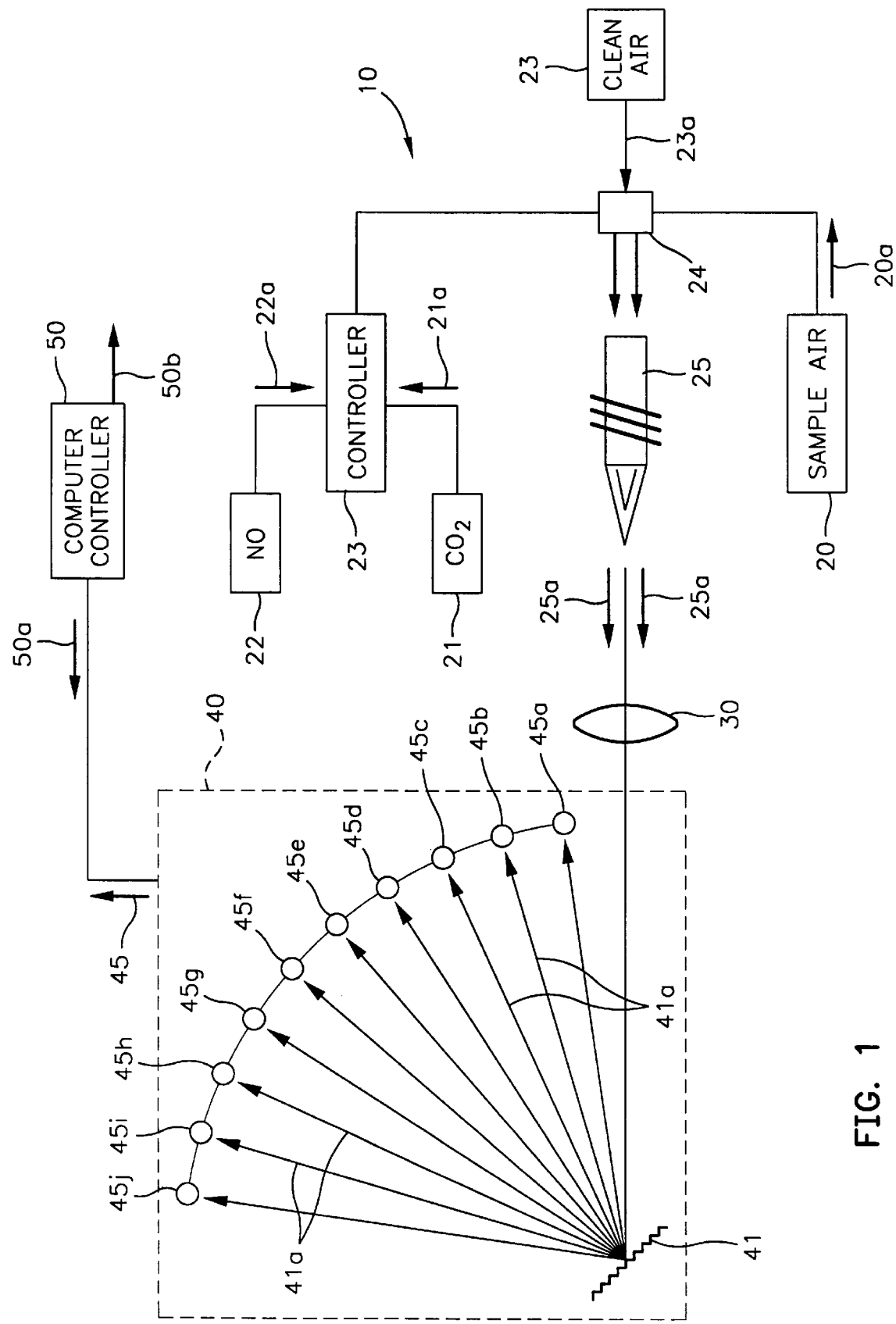
FIG. 1 is a schematic representation of the apparatus of the invention.

Referring to FIG. 1, an inductively coupled argon plasma (ICAP) spectrometer system 10 is adapted to perform analysis of molecular species, such as CN, that have emissions which overlap the emissions of atomic metals found, for example, in flue-gas air emitted from combustors. Although such systems traditionally are used for the analysis of metals in liquid samples such as waste water, this invention, and its predecessor disclosed in U.S. Pat. No. 5,596,405, describe a revolutionary application for ICAP spectrometer system 10 for the analysis of airborne metals.

FIG. 1 schematically illustrates system 10. Sample air source 20 feeds sample air 20a to argon plasma torch 25 and airborne metals are vaporized and excited in the hot argon plasma. The excited metal atoms emit light 25a at characteristic wavelengths and the intensity of emitted light 25a at each characteristic wavelength is directly proportional to the concentration of each metal in sample air 20a. Bottle 21 and bottle 22 respectively store quantities of carbon dioxide and nitric oxide (NO) that are fed individually, but not in combination as measured amounts of carbon dioxide 21a and Nitric Oxide 22a to plasma torch 25. The emissions attributed to other compounds or molecular species will be ignored for now and will be elaborated on below. Appropriate optics 30 receive emitted light 25a, collect it, and focus it into a multichannel optical spectrometer 40.

Multichannel optical spectrometer 40 is provided with diffraction grating 41 that angularly disperses diffracted light 41a light 20a according to wavelength in a manner similar to how a prism operates, but with much greater precision and resolution. Such diffraction gratings have been and are in widespread use. Having a determinable range of emissions to diffract, a designer is free to select a suitable unit from many offered in the art.

Diffracted light 41a is directed to a plurality of photodetectors 45a, 45b, 45c, 45d, 45e, 45f, 45g, 45h, 45i, and 45j which are each located at precise positions in multichannel optical spectrometer 40 to intercept the various wavelengths of diffracted light 41a. While 10 such photodetectors are referred to here, it is to be understood that any number of such devices could be used as needed by a job at hand. Each photodetector is dedicated to receive a particular portion of diffracted light 41a that is characteristic of a certain metal or other species since the various metals emit light at unique wavelengths. Each photodetector produces detector signals 45 representative of the intensity of diffracted light 41a that impinges upon it. Representative signals 45 from each photodetector are separated from each other and are transmitted to computer 50 for processing.

Detector signals 45 from all photodetectors 45a, 45b, 45c, 45d, 45e, 45f, 45g, 45h, 45i, and 45j are fed to computer controller 50. Computer performs 50 creates performs all calculations necessary to achieve quantitative analysis of the airborne metals and issues appropriate command signals 50a or feedback signals 50b to control a waste combustor, for example in accordance with its programmed operational instructions.

As mentioned above, the method of this invention addresses the spectral interference associated with all spectrally interfering molecular species. A noteworthy interfering molecular species is ascribed to the interference problem caused by CN species. This invention offers an effective means by which the spectral interference due to the CN species radical can be accounted for and subsequently subtracted from the apparent metal concentrations. Consequently, the method achieves the appropriate correction resulting in accurate measurement of the affected metals.

In fact, the most troublesome molecular spectral interferences thus far observed have been associated with the stable CN radical. CN is not a component of flue gas but rather, a nascent reaction product of carbon and nitrogen sources entering the plasma. Carbon dioxide concentrations of 5–10 percent in the flue gases of furnaces and incinerators are not uncommon, and concentrations as high as 20 percent are typical for cement kilns, Therefore, there is no shortage of carbon to react in the plasma with dissociated nitrogen from the sample air stream. In addition, nitrogen oxide ($NO_x$) pollutants also contribute nitrogen upon dissociation but otherwise, yield a rich emission spectrum in their own right, The correction of the interferences caused by CN is accomplished by first measuring, in the same spectrometer described above that is also used to measure metal emissions, the concentration of the interfering molecular species, or chemical precursor of such, in this case, CN. First, a characteristic CN emission band is identified and selected that does not overlap a characteristic metal emission wavelength and is used to analyze the concentration of CN. One of photodetectors 45a, 45b, 45c, 45d, 45e, 45f, 45g, 45h, 45i, and 45j is then installed in an appropriate position in multichannel optical spectrometer 40 to intercept CN emission at this selected wavelength and an electronic detector signal 45 is acquired in the same manner as is done for the various metal emissions.

To correlate the detected CN emission intensity with CN concentration, output signals from the appropriately located photodetector 45h, for example, must first be calibrated. However, since CN is a nascent reaction product in the plasma and does not naturally exist in air, a surrogate calibration species must be used. Carbon dioxide is the principal chemical precursor to the formation of CN and is the primary source of carbon for forming the CN molecular radical in the argon plasma although other carbon-containing gases also lead to the formation of CN, including carbon monoxide or hydrocarbons such as propane. However, carbon monoxide and hydrocarbon contributions are relatively negligible. Consequently, the correction method of this invention concerns itself with the use of carbon dioxide as a calibration source for CN emission instead of propane or carbon monoxide. Additionally, in accordance with this inventive concept, it has been determined that virtually all of the carbon monoxide (present only in trace quantities) that enters the plasma is decomposed and very little if any carbon monoxide emission occurs. What little carbon there is from the carbon monoxide contributes to form CN. In essence, this inventive concept concerns correction of spectral interferences from molecular species CN and NO and considers carbon dioxide as the source of carbon in sample stack gas as well as the calibration source.

Therefore, it has been found to be a simple matter to introduce varying known amounts of carbon dioxide (diluted with air) into the plasma and to record the associated CN emission intensity. In this manner, the CN spectrometer channel can be calibrated. Subsequently, as sample air from a smokestack enters the plasma, the exact amount of carbon dioxide in the air can be analyzed. (Since all of the carbon dioxide entering the plasma is converted to CN, the resulting CN concentration is directly related to the carbon dioxide concentration in the sample air stream).

The interfering spectral emissions attributed to a number of molecular species can and do interfere with monitoring a number of hazardous air pollutants (HAP). Among the nearly 200 chemical species presently targeted as hazardous air pollutants are 14 metals, including Ag, As, Ba, Be, Cd, Co, Cr, Hg, Mn, Ni, Pb, Sb, Se, and Tl. The following Table I of FIG. 2A lists the analytical wavelengths used for detection of these metals by the CEM of this invention.

The emission wavelengths of FIG. 2A were selected on the basis of efficiency of excitation and optimum sensitivity in mixed-gas plasma. The airborne metal analysis most impacted by CN spectral interferences are Ag, As, Hg, Pb, Sb, Se, and Tl. Other metals may be equally affected by CN spectral interferences. Ag, As, Hg, Pb, Sb, Se, and Tl are given special consideration here because currently these metals are closely monitored by local, state and federal environmental agencies. The spectral interferences on these metals are most pronounced when low airborne concentrations 100 :g/dry standard cubic meter (DSCM) are being measured, and the CN emission intensity and atomic emission intensity at a given wavelength may be of comparable magnitude. HAP metal concentrations in this range are of considerable regulatory significance.

Characteristic visible CN emission is most prominent at 421.6 nm. Abundant CN emission bands also occur throughout the ultraviolet region of the spectrum and either coincide directly, or are immediately adjacent to many of the most sensitive emission lines of the affected metals listed above. For many metals, the relatively broad CN emission bands overlap the atomic peaks and/or spectral positions traditionally selected for background measurements. In the latter instance, negative interferences of appreciable magnitude may arise. The magnitude of the negative interferences can often be reduced by judicious selection of wavelengths used for background measurement with respect to CN emission band structure.

In order to achieve the detection sensitivity demanded by this analysis, only the most intense emission lines for the various metals of interest are used. For this reason, the selection of alternate, interference-free lines of emission has not been a viable option. Consequently, it has proven to be more analytically effective therefore, to deal directly with the spectral interferences. Possibly, a spectrometer of higher spectral resolution might be used to add discrimination against relatively broad-band interfering radiation. This would favor sensing narrower atomic emission lines of the metals of interest. But, a more immediate need exists to implement a facile solution to the problem of molecular spectral interferences that affect existing spectrometers. A few illustrative examples of spectral interferences due to CN emissions in the plasma follow along with a description of an effective and innovative method for mitigating the effects of these interferences using existing hardware and software capabilities in ICAP spectrometer system 10.

In a variety of electrical, microwave, or radio frequency-induced discharges, multiple CN emission bands arise in the presence of carbon and nitrogen compounds, see R. W. B. Pearse and A. G. Gavdon, *The Identification of Molecular Spectra* (Chapman and Hall, London, 1976) 4th ed., p. 103. CN emission spectra has been previously recorded as a result of deliberate introduction of hydrocarbons into an argon ICP, see D. Truitt and J. W. Robinson, *Anal. Chim. Acta.* 51, 61 (1970).

In accordance with this inventive concept, however, the first instance of spectral interference has been noted that was caused by CN emission associated with the carbon dioxide component of air injected into an argon plasma. The magnitude of this interference is appreciable, and in some cases, surprisingly large. For the metal elements directly affected, the severity of the interference is inversely proportional to the sensitivity with which that metal element is detected in the mixed-gas plasma.

ICAP spectrometer system 10 as schematically depicted in FIG. 1 shows essential elements of a commercially available plasma instrument that was utilized in the practice of this invention. A Thermo Jarrell Ash 61E TRACE inductively coupled argon plasma (ICAP) simultaneous spectrometer was used in the present invention and includes two software packages, to enable its use, in a computer that is schematically depicted in FIG. 1 as computer 50. The primary software package is called "THERMOSPEC™" which allows manual operation of the ICAP spectrometer. Through a series of keystroke commands, all aspects of analysis including calibration, measurement of unknown samples, and storage of analysis data can be accomplished. The secondary software package, called "THERMO-SPEC™" COMMAND LANGUAGE is used to write command sequences that can used to entirely automate instrument operation. This is particularly useful in process analysis applications such as the present invention in which repetitive measurements are to be made at frequent intervals over long periods of time. Various command and timing sequences can be configured that can be used to eliminate the need for human instruction to the system. "THERMO-SPEC™" COMMAND LANGUAGE was applied in the present invention to not only control operation of ICAP spectrometer 40, but it also periodically triggers activation of the sampling interface portion of combination mixing-device-sampling-interface 24 to allow introduction of an unknown air sample into the plasma of plasma torch 25 for analysis. The "THERMOSPEC™" COMMAND LANGUAGE consists of a lexicon of individual commands that can be applied in a user-selected sequence to achieve the desired instrument and analysis functions. In this invention this lexicon was used to configure a complex series of command sequences specifically to accomplish the numerous functions that were required. The command sequences were configured by the inventor and, for that matter, could have been configured by anyone else of ordinary skill in the art having the teachings of this invention in mind.

The third software package for computer 50 involves the use of inventor-written programs in compiled BASIC language. BASIC is a high-level language that allows mathematical variables to be assigned to various measured and calculated parameters and allows calculations to be carried out. The BASIC language programs were written by the inventor, or for that matter, could have been written by anyone else of ordinary skill in the art having the teachings of this invention before him. These BASIC language programs permit communication between the computer and various components of the isokinetic sampling system to permit complete automation of this system. The BASIC language programs also permit the reading of user-configured data files containing critical parameter values necessary for the operation of the sampling system (please refer to "Method and Apparatus for Automated Isokinetic Sampling of Combustor Flue Gases for Continuous Monitoring of Hazardous Metal Emissions" by Michael Seltzer, U.S. Patent and Trademark Office Navy Case No.78564, filed Sep. 17, 1997) portion of combination mixing-device-sampling-interface 24. For example, these data files contain information such as the diameter of an isokinetic sampling nozzle, not shown, and the percent moisture in the flue gases, and other information not available either through external transducers or measurements. The BASIC language programs also perform tasks such as calculating the velocity of the flue gases and calculating the sample extraction flow rate required for 100 percent isokinetic extraction. The BASIC language programs also control the operation of the computer's analog to digital (A/D) converter, not shown, and it's digital to analog (D/A) converter, not shown, used to input and output certain voltage signals, respectively. For example, the A/D converter takes in a proportional voltage signal from a signal conditioner, not shown, that acquires the temperature of the sample air in the sample loop. The BASIC language program converts this proportional voltage to an actual temperature value and uses it in calculations. The D/A converter outputs a proportional voltage to adjust the mass flow controller, not shown, used to throttle the flow of extracted sample air in order to achieve isokinetic conditions at the point of sample extraction. The BASIC language program also uses parameters such as the sample air temperature, pressure, and moisture content to calculate a correction factor to be used by the "THERMOSPEC™" software to normalize the airborne metal concentrations to dry standard conditions (70 degrees F., 29.92 inches of mercury pressure). This factor, along with other parameters is then written to a second data file for later reading by "THERMOSPEC™" COMMAND LANGUAGE programs for subsequent application by "THERMOSPEC™".

BASIC language programs also serve other supporting functions such as manual control of sample extraction flow rate and manual calculation of flue gas velocity, sample extraction flow rate, and flue gas molecular weight. In the present invention, BASIC language programs are subservient to the "THERMOSPEC™" and "THERMOSPEC™" COMMAND LANGUAGE programs and are automatically executed as a result of certain commands used in the "THERMOSPEC™" COMMAND LANGUAGE sequences.

Undoubtedly, other high-level programming languages such as Fortran, Pascal, or C could be used in place of BASIC, given that they are compatible with existing hardware and software capabilities The Thermo Jarrell Ash (Franklin, Mass.) 61E TRACE inductively coupled argon plasma (ICAP) simultaneous spectrometer was used as the elemental analyzer component of the continuous emissions monitor (CEM) for multimetals. Salient features of the TRACE include an axially-mounted and viewed plasma torch (plasma torch 25) and a direct-reader polychromator or spectrometer, (corresponding to multichannel optical spectrometer 40). The polychromator contains a plurality of dedicated photodetectors (45a, 45b, 45c, 45d, 45e, 45f, 45g, 45h, 45i, and 45j), one for each metal element of interest to allow simultaneous detection of all metal elements of interest.

While the TRACE was chosen based on reputed sensitivity and durability, virtually any ICAP simultaneous spectrometer will suffice, given that its intrinsic sensitivity is satisfactory for the application in mind. Some simultaneous ICAP spectrometers do not employ a plurality of dedicated photodetectors, but instead, employ a solid state array detector such as a charge-injection device (CID) or a charge-coupled device (CCD) to intercept the diffracted atomic emission and differentiate between the various wavelengths by including hundreds or thousands of individual detector segments on the device substrate. An electrical signal, proportional to the light intensity striking each segment, can be acquired and associated with the metal element emitting that light.

Other ICAP spectrometers that are not simultaneous spectrometers are called scanning spectrometers. These spectrometers can only detect one metal element at a time and are required to scan from wavelength to wavelength to acquire the same information that a simultaneous spectrometer can obtain almost instantaneously. Consequently, the time penalty incurred by using a scanning spectrometer makes it impractical for performing in accordance with this invention which provides for continuous monitoring of airborne metals.

Spectral interferences associated with CN and NO emissions have been found to be identical in manifestation to those that arise from concomitant metals in samples. For example, a large number of well-documented spectral interferences occur as a result of direct-line overlap between iron emission and the emission lines of various analytes. In most cases, the extent of the interference, can be determined by measuring, in the absence of analyte, the magnitude of the apparent analyte concentration recorded as a result of the interfering emission associated with a given interferant concentration. A coefficient can then be calculated and stored for use in subsequent analyses to numerically account for the contribution of the interferant to the total analytical signal. Where multiple species interfere with an affected analyte, multiple coefficients can be applied. Most modern ICP spectrometers incorporate this feature into their operating software and corrections can be made automatically,. Thermospec™ software is designed to perform this operation as an interfering element correction (IEC) for traditional spectral interferences that arise from concomitant metals.

While traditional methods exist for correcting inter-element interferences, no such method has been demonstrated to accomplish correction of spectral interferences arising from airborne molecular species on affected analyte metals in argon plasma. Moreover, it has been observed that the magnitudes of inter-element interferences routinely encountered during the analysis of conventional liquid samples are not overwhelming, but are, however, worthy of attempts at correction.

Figure 3:
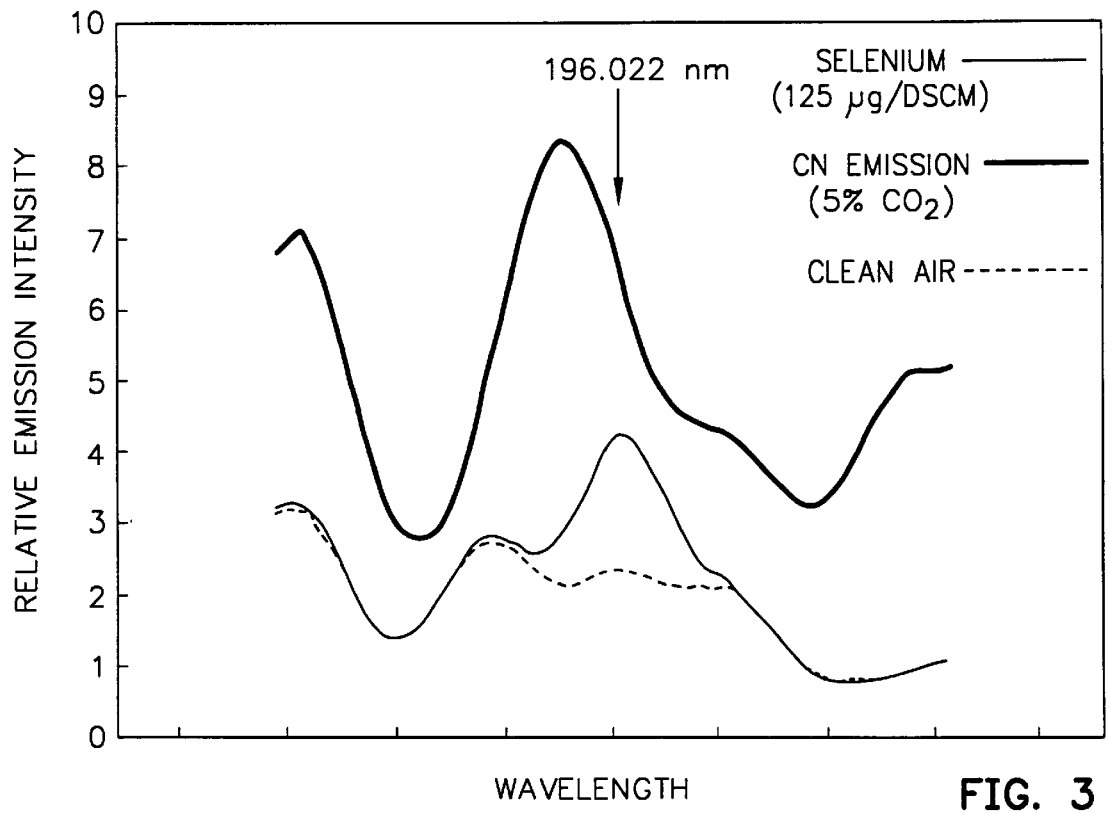
FIG. 3 depicts the relative intensities of emission for the molecular species CN and the metal selenium at and near 196.022 nm which is characteristic for selenium.

In contradistinction, this invention accomplishes the correction of spectral interferences arising from airborne molecular species in an argon plasma. The invention has this capability irrespective of the fact that the magnitudes of spectral interferences encountered during the analysis of airborne metals in flue gases, are of such considerable magnitudes that, if not directly accounted for, will compromise the quality of the measurements of the affected airborne metals. See FIG. 3 which depicts the relative intensities of emission for the molecular species CN and the metal selenium at and near 196.022 nm which is characteristic for selenium. The relative emissions depicted in FIG. 3 are typical. The emissions of many other metals are similarly interfered with by, not only this molecular species, but other species such as NO, as well. The invention also may correct for these spectral interferences.

Furthermore, the method of this invention differs from the previous techniques involving metals since it calls for simultaneous measurement of both CN and metal emission intensities, quantitation of the emitting species, and subsequent accounting for the interfering radiation appearing in each of the affected spectrometer channels.

Figure 4:
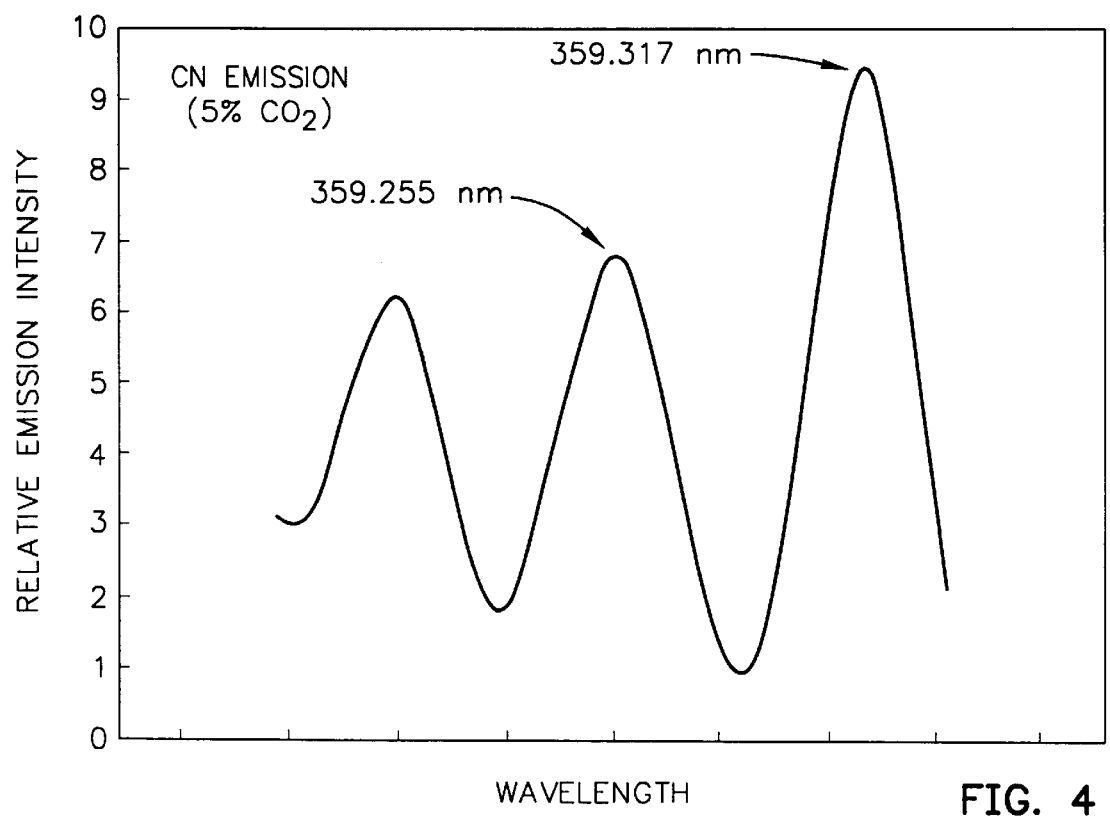
FIG. 4 shows CN band structure in the vicinity of the 359.255 nm line selected to facilitate interference correction.

CN emission bands are abundant in the spectral region between 170 and 420 nm thereby facilitating selection of an isolated CN band for interference correction purposes. Accordingly, a CN band is chosen that is not coincident with metal emission bands of appreciable intensity, especially metals likely to be found in flue gases. A direct reader spectrometer was used that featured pre-set exit slit positions for various elements along the Rowland circle. A position normally reserved for samarium at 359.260 nm was selected for detection of a CN emission band at 359.255 nm. A quartz refractor plate positioned in front of the exit slit was used to accomplish fine tuning. The use of the samarium position is not only convenient, but the likelihood of encountering samarium in flue gases is small. Although a more intense CN emission band is easily accessible at an adjacent wavelength of 359.317 nm, wing emission from a chromium line of appreciable intensity at 359.347 nm would have been problematic. FIG. 4 shows CN band structure in the vicinity of the 359.255 nm line selected for interference correction.

Figure 5:
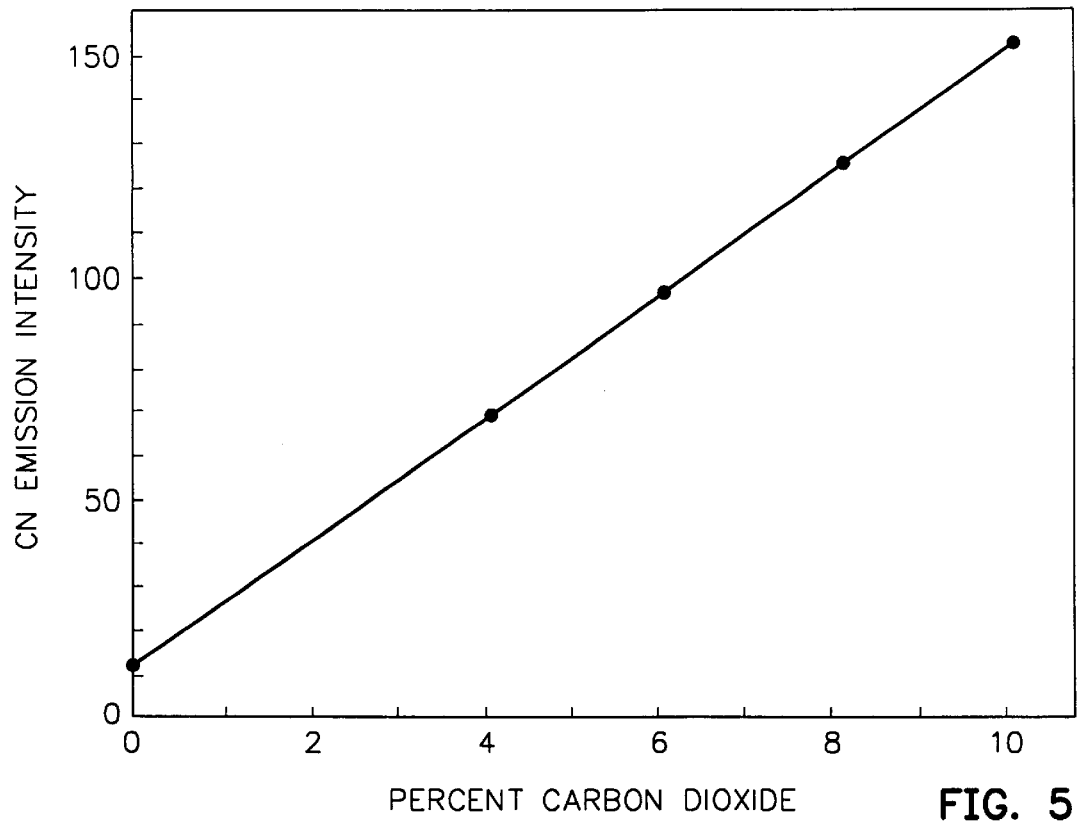
FIG. 5 illustrates the linear relationship between CN emission intensity and 4, 6, 8, and 10 percent concentrations of carbon dioxide in air.

Because CN is a nascent species in the plasma, a surrogate calibration source is necessary. Carbon dioxide is by far, the most significant precursor to CN formation in the plasma due to its abundance in the flue gas streams from which sample air is extracted and subsequently injected into the argon plasma. Introduction of an air stream containing carbon monoxide or any hydrocarbon into the plasma also results in the production of CN emission. By far, carbon dioxide is the least hazardous of these and is easily obtained, stored, and handled. Carbon dioxide has been selected therefore, as a surrogate calibration gas for the CN emission channel of the spectrometer. The calibration system consists of a lecture-size bottle of carbon dioxide 21, a pressure regulator, a precision needle valve, and a rotameter. The last three of these components are shown in FIG. 1 as controller 23. These components easily control the flow rate of carbon dioxide 21a so that it can be effectively used for calibration. Typically, flow rates of carbon dioxide 21a at 0.4, 0.6, 0.8 and 1.0 l/min. are transported to a combination mixing-device-sampling-interface 24. The mixing portion of device 24 allows dilution by ambient air 23a not having any metals in it from clean air source 23 to achieve a total flow of 10.0 l/min of air into the sampling interface portion of device 24 and into plasma torch 25. The resulting carbon dioxide concentrations are 4, 6, 8, and 10 percent, respectively. These concentrations produce representative CN emissions that can be collectively shown in a linear relationship. FIG. 5 illustrates the linear relationship between CN emission intensity and the above listed percentages of carbon dioxide in sample air.

To achieve satisfactory interference correction in this invention, it is essential that the detected interferant concentrations attributed to interfering molecular species, such as CN, are within the linear range of detection for that particular species. When a source in which higher $CO_2$ concentrations are encountered, such as a cement kiln, the calibration range can be expanded accordingly.

The channels consisting of appropriately positioning photodetectors for metals and CN species in spectrometer 40 are calibrated so that representative and characteristic emissions from the excited metals and CN species can be received. Replicate aliquots of sample air 20a containing an appropriate fraction of carbon dioxide are introduced into the plasma of plasma torch 25 through sampling interface 24 as described above. The detected CN emission intensities and corresponding $CO_2$ concentrations are recorded along with the apparent analyte concentrations for the affected metals. Interfering Element Concentration (IEC) coefficients are manually calculated in for each of the affected analyte metals using equation (1). Averaging the results of replicate measurements help minimize the possibility that an erroneous coefficient will be retained as a result of a single noisy measurement. The final coefficients are entered into a method file in computer 50 for use in subsequent analyses.

During each ensuing introduction of sample air 20a that is comprised of flue gases or stack air into the plasma of plasma torch 25, CN emission intensity in the plasma is measured and the corresponding $CO_2$ concentration is quantified. Correction for interference attributed to spectral interferences from the molecular species, such as CN, now may be achieved. Interference correction is achieved in computer 50 using equation (2). Equation (2) multiplies the detected concentration of $CO_2$ by the IEC coefficient for each affected element (atomic metal) to account for the contribution of the interfering emission to the apparent analyte concentration. This amount is then subtracted to obtain the interference corrected analyte concentration.

$$B_{IEC} = \frac{[\text{metal}]_{app}}{[CO_2]} \tag{1}$$

$$[\text{metal}]_{corr} = [\text{metal}]_{app} - (B_{IEC})[CO_2] \tag{2}$$

where:

$B_{IEC}$=IEC coefficient $[CO_2]$=measured $CO_2$ concentration $[\text{metal}]_{app}$=apparent metal analyte concentration $[\text{metal}]_{corr}$=corrected metal analyte concentration The method of this invention assures correction of CN spectral interference. This is evident when an examination is made of the efficacy of the interference correction method. Duplicate element channels are configured in the software that operates computer 50 and the associated elements of this invention. These duplicate channels use the same physical channel spectrometer hardware but do not employ interference corrections. Accordingly, for an affected metal analyte, both apparent and corrected concentrations are obtained. Table II of FIG. 2B summarizes the typical effectiveness of CN spectral interference correction for selected metal analytes.

Included in Table II are the stack-air detection limits for each analyte, IEC coefficients, apparent and corrected concentrations measured in the absence of any metals using a clean air stream containing nominally 5 and 10 percent carbon dioxide, respectively, and the percent correction achieved. The IEC coefficients in each case were determined previously by replicate measurements made during the introduction of air containing nominally 10 percent $CO_2$. For the seven elements listed in Table II, effective correction was achieved at both 5 and 10 percent $CO_2$ conditions with slight under-corrections and over-corrections made in certain instances. Failure to correct for the spectral interferences will result in either an over-estimate or, in some instances, an under estimate of true atomic metal concentrations. It is important to note that, in most cases, apparent metal concentrations were corrected to values that were significantly below the stack air detection limits previously documented using this instrumentation.

Figure 6:
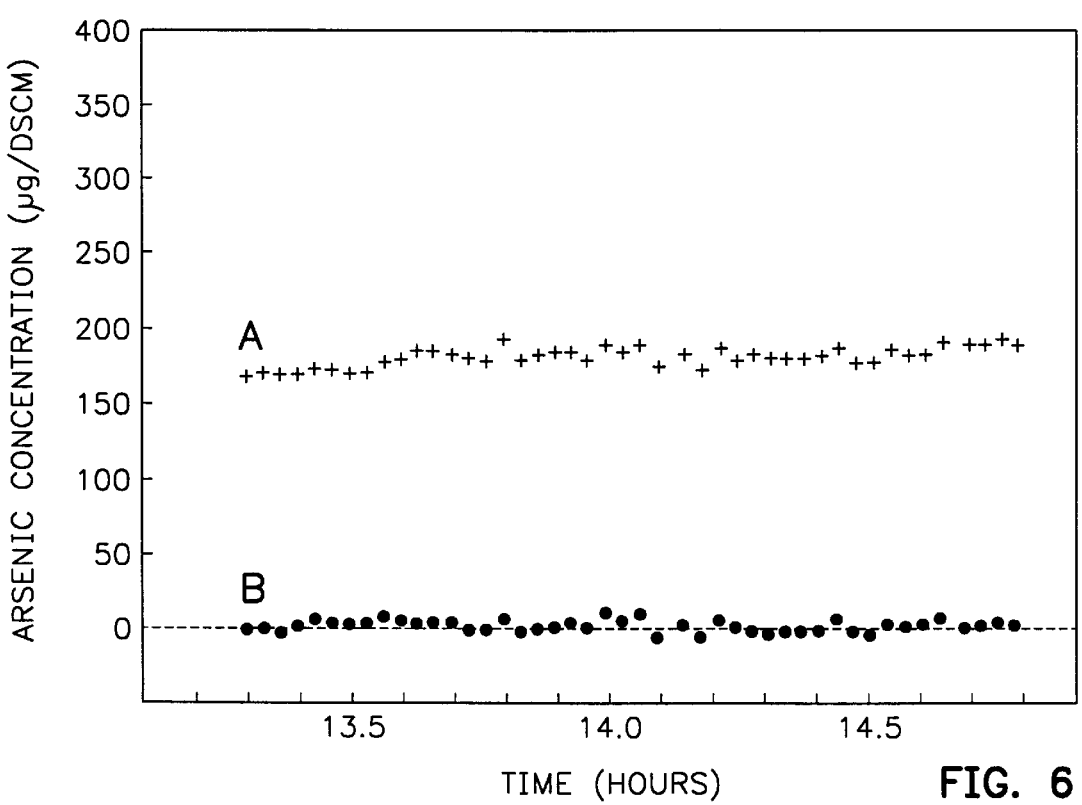
FIG. 6 illustrates the apparent arsenic concentration, expressed in micrograms per dry standard cubic meter (DSCM) detected in the emissions of flue gas from a rotary kiln of a deactivation furnace for explosive ordnance. The data of line A represents composite signals consisting of possible contributions from molecular species and arsenic. The data of line B illustrates the interference-corrected concentration or actual concentration of arsenic.

The method of this invention provides an effective correction of spectral interferences emitted from a stack of a combustor under monitoring conditions in the field. The true test of the effectiveness of the method of this invention is its performance in the analysis of real samples. Sample air was extracted from the stack of a working combustor over a prolonged period of time. FIG. 6 shows the apparent arsenic concentration, expressed in micrograms per dry standard cubic meter (DSCM), detected in the emissions of flue gas from a rotary kiln of a deactivation furnace for explosive ordnance. The data of line "A" represents composite signals consisting of possible contributions from both molecular species and arsenic that are recorded using the duplicate channel described above. Data of line "B" is representative of the actual concentration of arsenic. The data of line "B" result from automatic corrections for spectral interferences from CN emission.

Figure 7A:
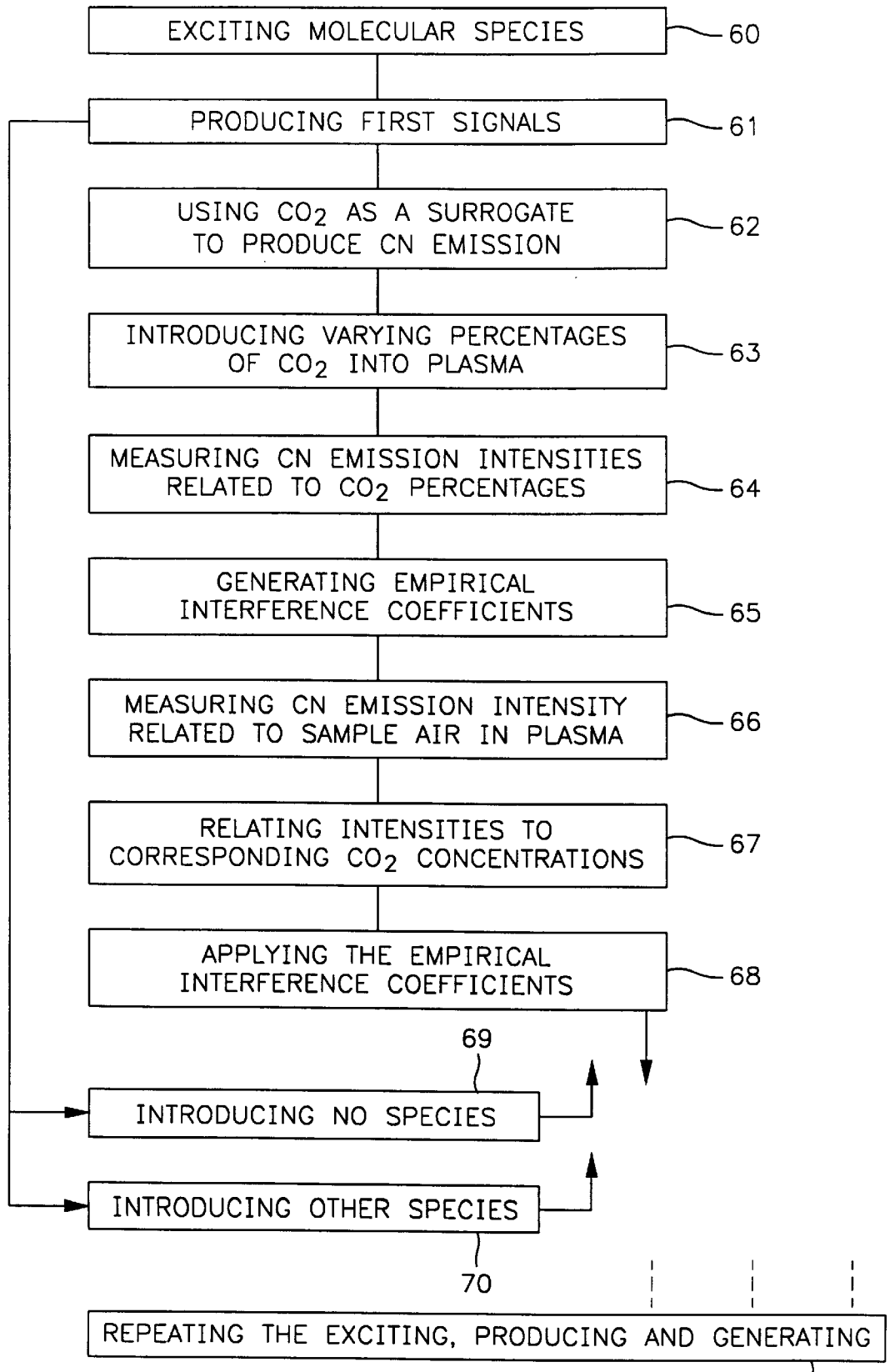
FIGS. 7A, 7B, and 8 schematically depict methods of this invention.

Referring to FIGS. 7A an 7B, the method of measuring spectral interferences affecting on-line detection of atomic metals includes exciting 60 molecular species in the absence of atomic metals in argon plasma receiving air to emit light at representative wavelengths. Producing 61 first signals representative of intensities of the emitted light at the representative wavelengths includes first spectral interference signals attributed to intensities of light representative of the molecular species that would coincide with light emitted at wavelengths characteristic of affected atomic metals to yield apparent concentrations of the affected atomic metals in the absence of the affected atomic metals, and first molecular species signals attributed to intensities of light emitted at one wavelength representative of the concentration of the molecular species only but distinct from wavelengths of emitted light characteristic of the affected atomic metals. The method further includes using 62 $CO_2$ as a surrogate source to produce CN emission in the plasma. $CO_2$ is quantitatively converted to CN since CN does not exist naturally but is a nascent reaction product between carbon and nitrogen in the plasma while nitrogen is a natural component of sample air. Introducing 63 varying percentages of $CO_2$ into the plasma precedes measuring 64 the corresponding CN emission intensities from the varying percentages of $CO_2$ to establish a linear calibration relationship between CN emission intensity and known $CO_2$ concentration. This allows generating 65 empirical interference coefficients representing the ratio of molecular species concentrations derived from the first molecular species signals to apparent concentrations for each of the affected atomic metals derived from the first spectral interference signals for each of the affected atomic metals. The foregoing facilitates measuring 66 CN emission intensities arising from the introduction of the sample air into the plasma and relating 67 those intensities to corresponding $CO_2$ concentrations.

Applying 68 the empirical interference coefficients accounts for contributions of molecular spectral interferences to apparent metal concentrations and determines net concentrations of the affected atomic metals in sample air. The empirical coefficients for each of the affected atomic metals relate the extent of spectral interferences manifested as apparent metal concentrations attributed to the molecular species with the concentration of the molecular species. The molecular species may be the nascent species CN created in argon plasma that is attributed to the presence of $CO_2$ in the argon plasma.

The method has the option of introducing 69 varying percentages of NO species into the plasma and measuring the corresponding emission intensities of NO to establish a linear calibration relationship between emission intensities of NO and known concentrations of NO. The method further has the option of introducing 70 varying percentages of other interfering molecular species into the plasma and measuring the corresponding emission intensities of other interfering molecular species to establish a linear calibration relationship between emission intensities of other interfering molecular species and known concentrations of other interfering molecular species.

Exciting 60 also may be the exciting of a plurality of molecular species including CN. The method further may include repeating 70 the steps of exciting 60 individual ones of the plurality of molecular species but without the affected atomic metals, producing 61 a plurality of first signals representative of intensities of emitted light for the individual ones of the plurality of molecular species, and generating a corresponding plurality of empirical interference coefficients for the affected ones of the atomic metals for each of the plurality of molecular species.

Figure 7B:
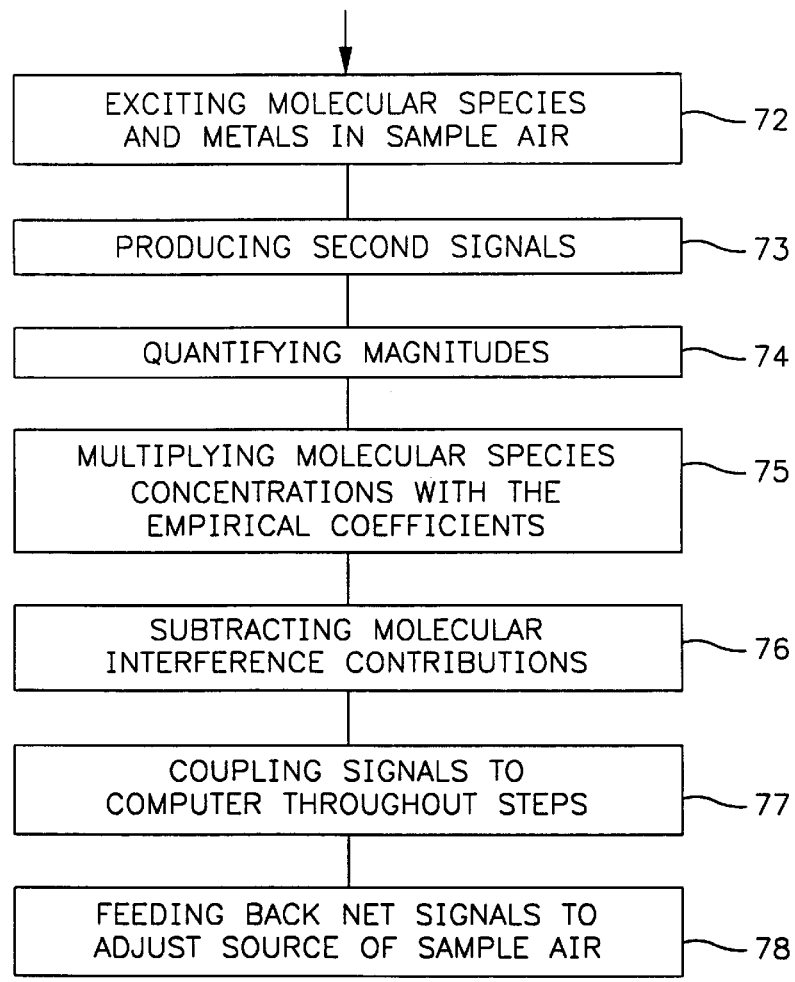

Referring again to FIGS. 7A and 7B, the step of applying 68 is elaborated on to include exciting 72 the affected atomic metals and the molecular species in sample air to emit light at wavelengths characteristic of the affected atomic metals and molecular species. The exciting of the affected atomic metals and the molecular species is in argon plasma. Producing 73 second signals that are representative of intensities of the emitted light at the characteristic wavelengths includes second molecular species signals corresponding to intensities of light characteristic of the concentration of the molecular species but distinct from wavelengths of emitted light characteristic the affected atomic metals. Producing 73 second signals also includes composite signals corresponding to the combined intensities of light emitted by the molecular species and the affected atomic metals at wavelengths characteristic of the affected atomic metals to provide apparent metal concentrations having possible contributions from both actual concentrations of the affected atomic metals and spectral interferences attributed to interfering molecular emissions. Quantifying 74 the magnitudes of the contributions of spectral interferences derived from the intensities of the light emitted by molecular species at wavelengths characteristic of the affected atomic metals to the apparent concentrations of the affected atomic metals involves multiplying 75 molecular species concentrations with the empirical coefficients to yield values representing the contributions from molecular interferences to the apparent metal concentrations. Subtracting 76 contributions from molecular interferences to total apparent concentrations of the affected atomic metals from the total apparent concentrations of affected atomic metals to yield net concentrations of the affected atomic metals in the sample air. The sample air is taken from gases emitted from stationary sources of combustion gases, such as, a waste incinerator, cement kiln, coal fired boiler, oil fired boiler or other combustion flue-gas source. Each of the atomic metals may be any of the group of atomic metals including, but not limited to, Ag, As, Ba, Be, Cd, Co, Cr, Hg, Mn, Ni, Pb, Sb, Se, and Tl and the exciting 72 may occur in a plasma torch.

The step of producing 73 includes diffracting light emitted from the plasma torch with a diffraction grating and detecting the diffracted light with a plurality of detectors that are each positioned to receive and detect a separate wavelength of the diffracted light. Coupling 77 the signals representative of intensities of emitted light at the characteristic wavelengths and at the representative wavelengths to a computer is effected throughout this method. The steps of generating 62, applying 63, quantifying 74, multiplying 75, and subtracting 76 are performed with the assistance of a computer so that net signals are created simultaneously and there can be feeding back 78 net signals to the source of the sample air to adjust the rate of introduction of waste into the source, thereby constituting a closed-loop process control arrangement.

Figure 8:
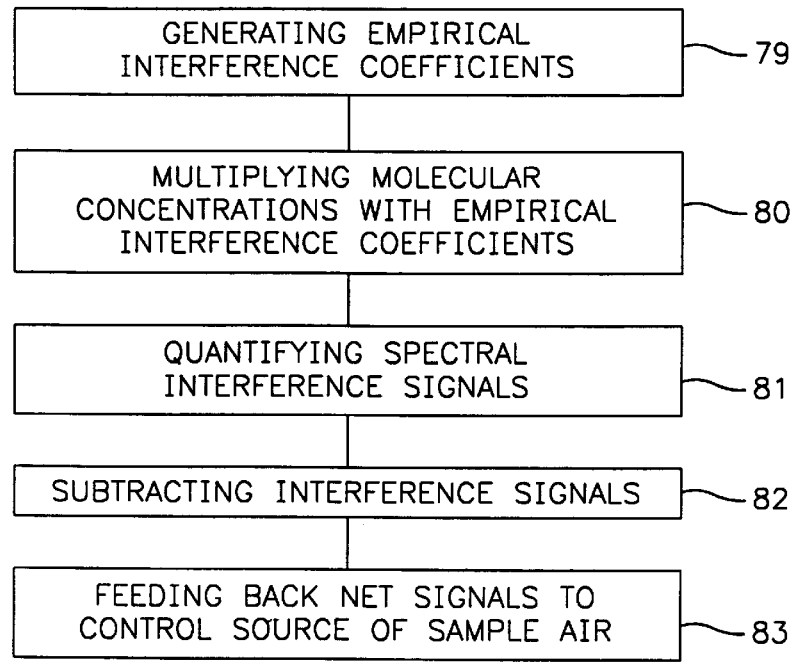

Referring to FIG. 8, a method of analyzing particulates in sample air excited in argon plasma includes generating 79 empirical interference coefficients for each of the affected atomic metals. The empirical interference coefficients represent the ratio of first molecular species concentrations derived from intensities of light emitted at one wavelength representative of only the molecular species to apparent metal concentrations associated with first spectral interference signals representative of intensities of light emitted at some wavelengths that coincide with wavelengths of emission for both the molecular species and the affected atomic metals for each of the affected atomic metals. The first molecular species signals are attributed to intensities of light emitted at one wavelength representative of the molecular species but distinct from wavelengths of emitted light characteristic of the affected ones of the atomic metals, and the first spectral interference signals are attributed to intensities of light emitted at some wavelengths representative of the molecular species that coincide with light emitted at wavelengths characteristic of the affected ones of the atomic metals. The method includes multiplying 80 molecular species concentrations derived from intensities of light emitted at one wavelength characteristic of the molecular species but distinct from wavelengths of emitted light characteristic the affected atomic metals with the empirical interference coefficients to quantify the magnitudes of the spectral interference signals. The method further includes quantifying 81 spectral interference signals attributed to intensities of light emitted at some wavelengths characteristic of molecular species that coincide with light emitted at wavelengths characteristic of affected ones of atomic metals and subtracting 82 the spectral interference signals from composite signals representative of the molecular species and the affected atomic metals to yield net signals representative of net concentrations of the affected atomic metals in the sample air. The composite signals are attributed to intensities of light emitted at wavelengths characteristic of the affected atomic metals and at some wavelengths characteristic of the molecular species concentrations derived from light emitted at wavelengths characteristic of the affected atomic metals. Feeding back 83 the net signals to a source of the sample air permits adjustment of the rate of introduction of waste into the source so that harmful levels of emissions can be moderated or, at least, reduced thus constituting a closed-loop process control arrangement.

It should be readily understood that many modifications and variations of the present invention are possible within the purview of the claimed invention. It is therefore to be understood that within the scope of the appended claims the invention may be practiced otherwise than as specifically described.

I claim:

1. A method of measuring spectral interferences by directly monitoring the emission intensity of the interfering species affecting on-line detection of all atomic metals comprising the steps of:

exciting molecular species in the absence of atomic metals in a source of excitation selected from the group consisting of inductively coupled argon plasmas, inductively coupled plasmas sustained on gases other than argon, microwave-induced plasmas, electrical spark plasmas, arc-induced plasmas, laser-induced plasmas and analytical combustion flames receiving air to emit light at representative wavelengths;

producing first signals representative of intensities of said emitted light at said representative wavelengths including first spectral interference signals attributed to intensities of light representative of said molecular species that would coincide with light emitted at wavelengths characteristic of affected said atomic metals to yield apparent concentrations of said affected atomic metals in the absence of said affected atomic metals, and first molecular species signals attributed to intensities of light emitted at one wavelength representative of the concentration of said molecular species only but distinct from wavelengths of emitted light characteristic of said affected atomic metals; and generating empirical interference coefficients representing the ratio of molecular species concentrations derived from said first molecular species signals to apparent concentrations for each of said affected atomic metals derived from said first spectral interference signals for each of said affected atomic metals.

2. A method according to claim 1 further including the step of:

applying said empirical interference coefficients to account for contributions of molecular spectral interferences to apparent metal concentrations and to determine net concentrations of said affected atomic metals in sample air.

3. A method according to claim 2 in which said empirical coefficients for each of said affected atomic metals relate the extent of spectral interferences manifested as apparent metal concentrations attributed to said molecular species with the concentration of said molecular species.

4. A method according to claim 3 in which said molecular species is nascent species CN created in said source of excitation and attributed to the presence of $CO_2$ in said source of excitation.

5. A method according to claim 4 further including the step of:

using $CO_2$ as a surrogate source to produce CN emission in said source of excitation, $CO_2$ being quantitatively converted to CN, CN not existing naturally but being a nascent reaction product between carbon and nitrogen in said source of excitation, and nitrogen being a natural component of said sample air;

introducing varying percentages of $CO_2$ into said source of excitation;

measuring the corresponding CN emission intensities from said varying percentages of $CO_2$ to establish a linear calibration relationship between CN emission intensity and known $CO_2$ concentration;

measuring CN emission intensities arising from the introduction of said sample air into said source of excitation; and relating those intensities to corresponding $CO_2$ concentrations.

6. A method according to claim 3 further including the step of:

introducing varying percentages of NO species into said source of excitation and measuring the corresponding emission intensities of NO to establish a linear calibration relationship between emission intensities of NO and known concentrations of NO.

7. A method according to claim 3 further including the step of:

introducing varying percentages of other interfering molecular species into said source of excitation and measuring the corresponding emission intensities of other interfering molecular species to establish a linear calibration relationship between emission intensities of other interfering molecular species and known concentrations of other interfering molecular species.

8. A method according to claim 4 in which said step of exciting is the exciting of a plurality of molecular species including CN.

9. A method according to claim 8 further including the step of:

repeating said steps of exciting individual ones of said plurality of molecular species but without said affected atomic metals, producing a plurality of first signals representative of intensities of said emitted light for said individual ones of said plurality of molecular species, and generating a corresponding plurality of empirical interference coefficients for said affected ones of said atomic metals for each of said plurality of molecular species.

10. A method according to claim 9 further comprising the steps of:

exciting said affected atomic metals and said molecular species in sample air to emit light at wavelengths characteristic of said affected atomic metals and molecular species, said exciting of said affected atomic metals and said molecular species being in said source of excitation;

producing second signals representative of intensities of said emitted light at said characteristic wavelengths including second molecular species signals corresponding to intensities of light characteristic of the concentration of said molecular species but distinct from wavelengths of emitted light characteristic of said affected atomic metals, and composite signals corresponding to the combined intensities of light emitted by said molecular species and said affected atomic metals at wavelengths characteristic of said affected atomic metals to provide apparent metal concentrations having possible contributions from both actual concentrations of said affected atomic metals and spectral interferences attributed to interfering molecular emissions;

quantifying the magnitudes of the contributions of spectral interferences derived from the intensities of the light emitted by said molecular species at wavelengths characteristic of said affected atomic metals to the apparent concentrations of said affected atomic metals;

multiplying said molecular species concentrations with said empirical coefficients to yield values representing said contributions from molecular interferences to said apparent metal concentrations; and subtracting said contributions from molecular interferences to total apparent concentrations of said affected atomic metals from the total apparent concentrations of affected atomic metals to yield net concentrations of said affected atomic metals in said sample air.

11. A method according to claim 10 in which said sample air is selected from the group of gases emitted from stationary sources of combustion gases consisting of waste incinerator, cement kiln, coal fired boiler, oil fired boiler and combustion flue-gas source.

12. A method according to claim 3 in which each of said atomic metals is selected from the group of atomic metals consisting of Ag, As, Ba, Be, Cd, Co, Cr, Hg, Mn, Ni, Pb, Sb, Se, and Tl.

13. A method according to claim 10 in which each of said atomic metals is selected from the group of atomic metals consisting of Ag, As, Ba, Be, Cd, Co, Cr, Hg, Mn, Ni, Pb, Sb, Se, and Tl.

14. A method according to claim 13 in which said steps of exciting occur in said source of excitation.

15. A method according to claim 12 in which said step of producing includes the steps of:

diffracting light emitted from said source of excitation with a diffraction grating; and detecting said diffracted light with a plurality of detectors each positioned to receive and detect a separate wavelength of said diffracted light.

16. A method according to claim 14 in which said steps of producing include the steps of:

diffracting light emitted from said source of excitation with a diffraction grating; and detecting said diffracted light with a plurality of detectors each positioned to receive and detect a separate wavelength of said diffracted light.

17. A method according to claim 15 further including the step of:

coupling said signals representative of intensities of said emitted light at said characteristic wavelengths and at said representative wavelengths to a computer.

18. A method according to claim 16 further including the step of:

coupling said signals representative of intensities of said emitted light at said characteristic wavelengths and at said representative wavelengths to a computer.

19. A method according to claim 17 in which said steps of generating, applying, and detecting are performed with the assistance of a computer.

20. A method according to claim 18 in which said steps of generating, applying, quantifying, multiplying, and subtracting are performed with the assistance of a computer.

21. A method according to claim 10 in which said net concentrations of said affected atomic metals are created simultaneously.

22. A method according to claim 19 in which said net concentrations of said affected atomic metals are created simultaneously.

23. A method according to claim 10 further including the step of:

feeding back said net concentrations of said affected atomic metals to a source of said sample air to adjust the rate of introduction of waste into said source.

24. A method according to claim 22 further including the step of:

feeding back said net concentrations of said affected atomic metals to a source of said sample air to adjust the rate of introduction of waste into said source.

25. A method of analyzing particulates in sample air in a source of excitation selected from the group consisting of inductively coupled argon plasmas, inductively coupled plasmas sustained on gases other than argon, microwave-induced plasmas, electrical spark plasmas, arc-induced plasmas, laser-induced plasmas and analytical combustion flames comprising the steps of:

quantifying spectral interference signals attributed to intensities of light emitted at some wavelengths characteristic of molecular species that coincide with light emitted at wavelengths characteristic of affected ones of atomic metals; and subtracting said spectral interference signals from composite signals representative of said molecular species and said affected atomic metals to yield net signals representative of net concentrations of said affected atomic metals in said sample air.

26. A method according to claim 25 in which said step of quantifying includes the step of:

multiplying molecular species concentrations derived from intensities of light emitted at one wavelength characteristic of said molecular species but distinct from wavelengths of emitted light characteristic said affected atomic metals with empirical interference coefficients to quantify the magnitude of said spectral interference signals.

27. A method according to claim 26 in which said composite signals are attributed to intensities of light emitted at wavelengths characteristic of said affected atomic metals and at some wavelengths characteristic of said molecular species that coincide with light emitted at wavelengths characteristic of said affected atomic metals.

28. A method according to claim 25 in which said step of quantifying includes the step of:

generating empirical interference coefficients that represent the ratio of first molecular species concentrations derived from intensities of light emitted at one wavelength representative of only said molecular species to apparent metal concentrations associated with first spectral interference signals representative of intensities of light emitted at some wavelengths that coincide with wavelengths of emission for both said molecular species and said affected atomic metals for each of said affected atomic metals.

29. A method according to claim 28 in which said first molecular species signals are attributed to intensities of light emitted at one wavelength representative of said molecular species but distinct from wavelengths of emitted light characteristic of said affected ones of said atomic metals, and first spectral interference signals are attributed to intensities of light emitted at some wavelengths representative of said molecular species that coincide with light emitted at wavelengths characteristic of said affected ones of said atomic metals.

30. A method according to claim 29 further including the step of:

feeding back said net signals to a source of said sample air to adjust rate of introduction of waste into said source thereby constituting a closed-loop process control arrangement.

31. A method of measuring spectral interferences attributed to CN species to enable detection of atomic metals comprising the steps of:

exciting CN species in the absence of atomic metals in a source of excitation selected from the group consisting of inductively coupled argon plasmas, inductively coupled plasmas sustained on gases other than argon, microwave-induced plasmas, electrical spark plasmas, arc-induced plasmas, laser-induced plasmas and analytical combustion flames receiving air to emit light at representative wavelengths;

producing first signals representative of intensities of said emitted light at said representative wavelengths including first spectral interference signals attributed to intensities of light representative of said CN species that would coincide with light emitted at wavelengths characteristic of affected said atomic metals to yield apparent concentrations of said affected atomic metals in the absence of said affected atomic metals, and first CN species signals attributed to intensities of light emitted at one wavelength representative of the concentration of said CN species only but distinct from wavelengths of emitted light characteristic of said affected atomic metals; and generating empirical interference coefficients representing the ratio of CN species concentrations derived from said first CN species signals to apparent concentrations for each of said affected atomic metals derived from said first spectral interference signals for each of said affected atomic metals.

32. A method according to claim 31 further comprising the step of:

applying said empirical interference coefficients to account for contributions of CN spectral interferences to apparent metal concentrations and to determine net concentrations of said affected atomic metals in sample air.

33. A method according to claim 32 further comprising the steps of:

exciting said affected atomic metals and said CN species from sample air to emit light at wavelengths characteristic of said affected atomic metals and CN species, said exciting of said affected atomic metals and said CN species being in said source of excitation;

producing second signals representative of intensities of said emitted light at said characteristic wavelengths including second CN species signals attributed to intensities of light emitted at said one wavelength characteristic of said CN species but distinct from wavelengths of emitted light characteristic said affected atomic metals, and composite signals attributed to intensities of light emitted at wavelengths characteristic of said affected atomic metals and at some wavelengths characteristic of said CN species that coincide with light emitted at wavelengths characteristic of said affected ones of said atomic metals;

quantifying the magnitudes of the contributions of spectral interferences derived from the intensities of the light emitted by said molecular species at wavelengths characteristic of said affected atomic metals to the apparent concentrations of said affected atomic metals;

multiplying said molecular species concentrations with said empirical coefficients to yield values representing said contributions from molecular interferences to apparent metal concentrations; and subtracting said contributions from molecular interferences to total apparent concentrations of said affected atomic metals from the total apparent concentrations of affected atomic metals to yield net concentrations of said affected atomic metals in said sample air.

* * * * *